(12) United States Patent
Schnabel et al.

(10) Patent No.: US 10,231,449 B2
(45) Date of Patent: Mar. 19, 2019

(54) ALKOXYLATED POLYALKYLENEIMINES AS DISPERSANTS FOR AGROCHEMICAL FORMULATIONS

(75) Inventors: Gerhard Schnabel, Elsenfeld (DE); Paul Klingelhoefer, Mannheim (DE)

(73) Assignee: BASF SE, Ludwigshafen (DE)

( * ) Notice: Subject to any disclaimer, the term of this patent is extended or adjusted under 35 U.S.C. 154(b) by 69 days.

(21) Appl. No.: 14/122,483

(22) PCT Filed: May 21, 2012

(86) PCT No.: PCT/EP2012/059369
§ 371 (c)(1),
(2), (4) Date: Nov. 26, 2013

(87) PCT Pub. No.: WO2012/163709
PCT Pub. Date: Dec. 6, 2012

(65) Prior Publication Data
US 2014/0106965 A1    Apr. 17, 2014

Related U.S. Application Data

(60) Provisional application No. 61/490,625, filed on May 27, 2011.

(30) Foreign Application Priority Data

May 27, 2011   (EP) ..................................... 11167898

(51) Int. Cl.
| | | |
|---|---|---|
| *A01N 25/30* | (2006.01) | |
| *A01N 25/22* | (2006.01) | |
| *A01N 25/02* | (2006.01) | |
| *A01N 25/04* | (2006.01) | |
| *A01N 57/20* | (2006.01) | |
| *A01C 1/06* | (2006.01) | |
| *A01N 43/56* | (2006.01) | |

(52) U.S. Cl.
CPC ................ *A01N 25/22* (2013.01); *A01C 1/06* (2013.01); *A01N 25/02* (2013.01); *A01N 25/04* (2013.01); *A01N 25/30* (2013.01); *A01N 43/56* (2013.01); *A01N 57/20* (2013.01)

(58) Field of Classification Search
CPC ......... A01N 25/02; A01N 25/22; A01N 25/30
See application file for complete search history.

(56) References Cited

U.S. PATENT DOCUMENTS

| | | | |
|---|---|---|---|
| 6,156,720 A | 12/2000 | Boeckh et al. | |
| 6,300,304 B1 | 10/2001 | Boeckh et al. | |
| 2006/0040828 A1* | 2/2006 | Mao et al. | ..................... 504/365 |
| 2008/0171658 A1 | 7/2008 | Dyllick-Brenzinger et al. | |

FOREIGN PATENT DOCUMENTS

| | | | |
|---|---|---|---|
| WO | WO 99/67352 | 12/1999 | |
| WO | WO 2006/086485 | 8/2006 | |
| WO | WO 2006/094978 | 9/2006 | |
| WO | WO 2011/019652 | 2/2011 | |
| WO | WO2011/085067 | * | 7/2011 |

OTHER PUBLICATIONS

Extoxnet (http://extoxnet.orst.edu/pips/triclopy.htm, Jun. 1996).*
International Preliminary Report on Patentability dated May 28, 2013, prepared in International Application No. PCT/EP2012/059369.
International Search Report dated Aug. 28, 2012, prepared in International Application No. PCT/EP2012/059369.

* cited by examiner

*Primary Examiner* — Johann R Richter
*Assistant Examiner* — Danielle Sullivan
(74) *Attorney, Agent, or Firm* — Brinks Gilson & Lione

(57) ABSTRACT

The present invention relates to a composition comprising a water-insoluble pesticide and an alkoxylated polyalkyleneimine. The invention furthermore relates to a method of preparing this composition; to the use of this composition for dispersing agrochemical active substances; to a method of controlling phytopathogenic fungi and/or undesired plant growth and/or undesired insect or mite attack and/or for regulating the growth of plants, wherein the composition is allowed to act on the respective pests, their environment or the crop plants to be protected from the respective pest, on the soil and/or on undesired plants and/or on the crop plants and/or on their environment; and furthermore to seed comprising the composition.

12 Claims, No Drawings

ALKOXYLATED POLYALKYLENEIMINES AS DISPERSANTS FOR AGROCHEMICAL FORMULATIONS

This application is a National Stage application of International Application No. PCT/EP2012/059369, filed May 21, 2012, which claims the benefit of U.S. Provisional Application No. 61/490,625, filed May 27, 2011, the entire contents of which are hereby incorporated herein by reference. This application also claims priority under 35 U.S.C. § 119 to European Patent Application No. 11167898.3, filed May 27, 2011, the entire contents of which are hereby incorporated herein by reference.

The present invention relates to a composition comprising a water-insoluble pesticide and an alkoxylated polyalkyleneimine. The invention furthermore relates to a process for the preparation of this composition; to the use of this composition for dispersing agrochemical active substances; to a method of controlling phytopathogenic fungi and/or undesired plant growth and/or undesired insect or mite attack and/or for regulating the growth of plants, wherein the composition is allowed to act on the respective pests, their environment or the plants to be protected from the respective pest, on the soil and/or on undesired plants and/or on the crop plants and/or their environment; and furthermore to seed comprising the composition. The present invention comprises combinations of preferred features with other preferred features.

A wide range of polymers are known as dispersants for agricultural formulations:

WO 2011/019652 discloses, in claim 43, a formulation comprising auxin herbicides and an alkoxylated polyalkyleneimine. The formulation can comprise further co-herbicides. The alkoxylated polyalkyleneimines can, according to paragraph [53], be functionalized by reacting polyalkyleneimine with 1-100 mol equivalents ethylene oxide and 1-100 mol equivalents propylene oxide.

WO2006/094978 discloses a method for preparing an aqueous miniemulsion comprising a pesticide.

Disadvantages of the prior art are, inter alia, that no high storage stability of the formulation is achieved by the known dispersants; that the particle size growth of dispersed agrochemical active substances is not slowed down or suppressed; that the agglomeration of dispersed agrochemical active substances is not slowed down or suppressed; that the settling of dispersed agrochemical active substances is not slowed down or suppressed; and that abovementioned advantages manifest themselves in particular in the presence of high salt concentrations. It was therefore an object to overcome these disadvantages.

The object was achieved by a composition comprising a water-insoluble pesticide and an alkoxylated polyalkyleneimine.

Alkoxylated polyalkyleneimines are generally known, for example from WO2006/086492, WO 2007/135645 and WO 1999/67352. Usually, they have the general formula (I)

(I)

Here, alkylene oxide units undergo an additional reaction with the nitrogen atoms of the polyalkyleneimine main chain, where the main chains, before subsequently being modified, comprise primary, secondary and tertiary amine nitrogen atoms linked via linking units R. The main chains consist essentially of three types of units which can be distributed randomly along the chain. In the case of the units which account for the polyalkyleneimine main chains, they take the form of a) primary units, corresponding to the formula [H₂N—R]— and —NH₂, which terminate the main chain and any branching, b) secondary amine units corresponding to the formula —[NH—R]—, whose hydrogen atom is, after the modification, replaced by alkylene oxide units (for example 1 to 10 propyleneoxy units, butyleneoxy units and their mixtures, followed by 10 to 40 ethyleneoxy units), and c) tertiary amine units, corresponding to the formula

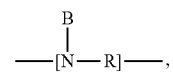

which constitutes the branching sites of the main and of the secondary backbone chains, with B representing a continuation of the chain structure by branching. The tertiary units do not have a replaceable hydrogen atom and are therefore not modified by substitution with an alkyleneoxy unit.

During the formation of the polyamine main chains, cyclization may occur, which is why a proportion of cyclic polyamine may be present in the basic polyalkyleneimine main-chain mixture. Each primary and secondary amine unit of the cyclic alkyleneimines is modified in the same manner as linear and branched polyalkyleneimines, which is by addition of the alkyleneoxy units.

R is linear $C_2$-$C_6$-alkylene, branched $C_3$-$C_6$-alkylene and their mixtures. The preferred branched alkylene is 1,2-propylene. The preferred R is ethylene. The preferred polyalkyleneimines have main chains which contain the same unit R, for example all units are ethylene. The main chain very specially preferably comprises exclusively ethylene units as R.

The molecular weight of the polyalkyleneimine main chain is preferably at least 600 daltons, preferably at least 1200 daltons, particularly preferably at least 1800 daltons, very specially preferably at least 2000 daltons to 25 000 daltons, preferably up to 20 000 daltons, especially preferably up to 15 000 daltons, very specially preferably 8000 daltons.

The polyalkyleneimines have been modified by substituting N—H units by an alkyleneoxy unit E. Examples of alkylene oxide units are $C_2$-$C_6$-alkylene oxide units such as ethylene oxide, propylene oxide or butylene oxide. It is preferred that at least one propyleneoxy or butyleneoxy unit will undergo an addition reaction with the nitrogen units of the main chain before substitution with a different alkyleneoxy unit takes place.

The alkoxylated polyalkyleneimine is preferably an ethoxylated and/or propoxylated polyalkyleneimine (such as polyethyleneimine), where it is especially preferred that the polyalkyleneimine has first been modified with propylene oxide units and subsequently with ethylene oxide units. The alkoxylated polyalkyleneimine is especially preferably an ethoxylated and propoxylated polyethyleneimine comprising from 1 to 50 mol of propylene oxide units and from 1 to 50 mol of ethylene oxide units, in each case per mol of NH units. The alkoxylated polyalkyleneimine is specially preferably an ethoxylated and propoxylated polyethyleneimine comprising 1.5 to 15 mol of propylene oxide and 1 to 50 mol of ethylene oxide, in each case per mol of NH units.

Preferred alkyleneoxy unit corresponding to the formula —$(R^1O)_m(R^2O)_nR^3$ where $R^1$ is prop-1,2-ylene, but-1,2-ylene or their mixtures (preferably prop-1,2-ylene), $R^2$ is ethylene, $R^3$ is hydrogen, $C_1$-$C_6$ alkyl, $C_2$-$C_6$ alkenyl, $C_2$-$C_6$ alkynyl, —$SO_3R^a$, —$P(O)OR^bOR^c$, —$CH_2CO_2R^d$, or —$C(O)R^e$, $R^a$ and $R^d$ independently of one another are an H, inorganic or organic cations, $R^b$ and $R^c$ independently of one another are an H, inorganic or organic cations, $C_1$-$C_6$-alkyl, $C_2$-$C_6$-alkenyl or $C_2$-$C_6$-alkynyl, $R^e$ is $C_1$-$C_{22}$-alkyl, $C_2$-$C_{22}$-alkenyl, $C_2$-$C_{22}$-alkynyl, $C_6$-$C_{22}$-aryl, $C_7$-$C_{22}$-alkylaryl.

$R^3$ is preferably an H or $C_1$-$C_6$-alkyl, especially preferably an H or methyl, in particular H.

$R^a$ and $R^d$ independently of one another are H, or are inorganic or organic cations which may carry one or more positive charges. Examples of inorganic cations are cations of ammonium, Na+, K+, $Mg^{2+}$, $Ca^{2+}$, or $Zn^{2+}$. Examples of organic cations are methylammonium, dimethylammonium, trimethylammonium, tetramethylammonium, (2-hydroxyethyl)ammonium, bis(2-hydroxyethyl)ammonium, tris(2-hydroxyethyl)ammonium, tetra (2-hydroxyethyl)ammonium. Preferably, $R^a$ and $R^d$ independently of one another are H or inorganic cations. If an inorganic or organic cation is present, then the matching anionic group would be formed on $R^3$ by the corresponding functional group (for example —$SO_3^-$, —$P(O)O^-O^-$ or —$CH_2CO_2^-$).

$R^b$ and $R^c$ preferably independently of one another are H, inorganic or organic cations. Suitable inorganic or organic cations are those mentioned under $R^a$.

$R^e$ is preferably $C_1$-$C_{12}$-alkyl, $C_6$-$C_{12}$-aryl or $C_7$-$C_{12}$-alkylaryl, especially preferably $C_1$-$C_6$-alkyl.

The index m has a value of at least 1, preferably at least 2 to 10, preferably up to 6, especially preferably up to 5. The index n has a value of at least 10, preferably at least 15, especially preferably at least 20 to 40, preferably up to 35, especially preferably up to 30. The total of m+n preferably has a value of at least 12, especially preferably at least 15, very especially preferably at least 20 to 40, especially preferably up to 35.

The molecular weight of the alkoxylated polyalkyleneimines is preferably at least 800 daltons, preferably at least 1200 daltons, especially preferably at least 1800 daltons, very specially preferably at least 2000 daltons to 25 000 daltons, preferably up to 20 000 daltons, especially preferably up to 15 000 daltons, very specially preferably 10 000 daltons.

The alkoxylated polyalkyleneimines may be nonionic or anionic compounds. Preferably, the alkoxylated polyalkyleneimines are nonionic compounds.

The alkoxylated polyalkyleneimines may comprise amino groups, which are selected from the group consisting of primary, secondary or tertiary amino groups. The alkoxylated polyalkyleneimines are preferably free of quaternary amino groups.

The preparation of the alkoxylated polyalkylimines is generally known, for example as described in WO 1999/67352 page 4, line 45 to page 6, line 42.

The alkoxylated polyalkylimine is usually soluble in water, for example to at least 5 g/l at 20° C. (preferably to at least 20 g/l, in particular at least 50 g/l). The alkoxylated polyalkylimine is preferably present in dissolved form in the composition according to the invention.

The composition according to the invention usually comprises at least 0.1% by weight, preferably at least 1% by weight and in particular at least 2% by weight of the alkoxylated polyalkylimine. The composition according to the invention usually comprises from 0.1 to 25% by weight, preferably from 0.5 to 15% by weight and in particular from 1 to 10% by weight of the alkoxylated polyalkylimine.

The term pesticides refers to at least one active substance selected from the group of the fungicides, insecticides, nematicides, herbicides, safeners and/or growth regulators. Preferred pesticides are fungicides, insecticides, herbicides and growth regulators. Especially preferred pesticides are herbicides. Mixtures of pesticides from two or more of the abovementioned classes may also be used. The skilled worker is familiar with such pesticides, which can be found, for example, in Pesticide Manual, 15th Ed. (2009), The British Crop Protection Council, London. The following pesticides are suitable, by way of example (pesticides A) to K) are fungicides):

A) Respiration Inhibitors complex-III-inhibitors at the $Q_o$-site (for example strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, methyl 2-[2-(2,5-dimethylphenyloxymethyl)phenyl]-3-methoxyacrylate, 2-(2-(3-(2,6-dichlorophenyl)-1-methylallylideneaminooxymethyl)phenyl)-2-methoxyimino-N-methylacetamide, pyribencarb, triclopyricarb/chlorodincarb, famoxadon, fenamidon;

complex-III-inhibitors at the $Q_i$-site: cyazofamid, amisulbrom;

complex-II-inhibitors (for example carboxamides): benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthio-biphenyl-2-yl)-3-difluoromethyl-1-methyl-1H-pyrazole-4-carboxamide, N-(2-(1,3,3-trimethylbutyl)phenyl)-1,3-dimethyl-5-fluoro-1H-pyrazole-4-carboxamide and N-[9-(dichloromethylene)-1,2,3,4-tetrahydro-1,4-methanonaphthalen-5-yl]-3-(difluoromethyl)-1-methyl-1H-pyrazole-4-carboxamide;

other respiration inhibitors (for example complex I, decouplers): diflumetorim; nitrophenyl derivatives: binapacryl, dinobuton, dinocap, fluazinam; ferimzone; organometal compounds: fentin salts such as fentin acetate, fentin chloride or fentine hydroxide; ametoctradin; and silthiofam;

B) Sterol Biosynthesis Inhibitors (SBI Fungicides)

C14-demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole; imidazoles: imazalil, pefurazoate, prochloraz, triflumizole; pyrimidines, pyridines and piperazines: fenarimol, nuarimol, pyrifenox, triforine;

delta14-reductase inhibitors: aldimorph, dodemorph, dodemorph acetate, fenpropimorph, tridemorph, fenpropidin, piperalin, spiroxamine;

3-ketoreductase inhibitors: fenhexamid;

C) Nucleic Acid Synthesis Inhibitors phenylamides or acylamino acid fungicides: benalaxyl, benalaxyl-m, kiralaxyl, metalaxyl, metalaxyl-M (mefenoxam), ofurace, oxadixyl;

others: hymexazole, octhilinone, oxolinic acid, bupirimate;

D) Cell Division and Cytoskeleton Inhibitors tubulin inhibitors such as benzimidazoles, thiophanates: benomyl, carbendazim, fuberidazole, thiabendazole, thiophanate-methyl; triazolopyrimidines: 5-chloro-7-(4-methyl-piperidin-1-yl)-6-(2,4,6-trifluorophenyl)-[1,2,4]triazolo[1,5-a]pyrimidine;

further cell division inhibitors: diethofencarb, ethaboxam, pencycuron, fluopicolid, zoxamid, metrafenon, pyriofenon;

E) Amino Acid Synthesis and Protein Synthesis Inhibitors methionine synthesis inhibitors (anilinopyrimidines): cyprodinil, mepanipyrim, pyrimethanil;

protein synthesis inhibitors: blasticidin-S, kasugamycin, kasugamycin hydrochloride hydrate, mildiomycin, streptomycin, oxytetracyclin, polyoxin, validamycin A;

F) Signal Transduction Inhibitors

MAP/histidine kinase inhibitors: fluoroimide, iprodione, procymidone, vinclozolin, fenpiclonil, fludioxonil;

G-protein inhibitors: quinoxyfen;

G) Lipid and Membrane Synthesis Inhibitors phospholipid biosynthesis inhibitors: edifenphos, iprobenfos, pyrazophos, isoprothiolane;

lipid peroxidation: dicloran, quintozene, tecnazene, tolclofos-methyl, biphenyl, chloroneb, etridiazole;

phospholipid biosynthesis and cell wall attachment: dimethomorph, flumorph, mandipropamid, pyrimorph, benthiavalicarb, iprovalicarb, valifenalate and 4-fluorophenyl N-(1-(1-(4-cyanophenyl)ethanesulfonyl)but-2-yl)carbamate;

compounds which affect cell membrane permeability and fatty acids: propamocarb, propamocarb hydrochloride H) "Multi-Site" Inhibitors inorganic active substances: Bordeaux mixture, copper acetate, copper hydroxide, copper oxychloride, basic copper sulfate, sulfur;

thio- and dithiocarbamates: ferbam, mancozeb, maneb, metam, metiram, propineb, thiram, zineb, ziram;

organochlorine compounds (for example phthalimides, sulfamides, chloronitriles): anilazine, chlorothalonil, captafol, captan, folpet, dichlofluanid, dichlorophen, flusulfamide, hexachlorobenzene, pentachlorophenol and its salts, phthalid, tolylfluanid, N-(4-chloro-2-nitrophenyl)-N-ethyl-4-methylbenzenesulfonamide;

guanidines and others: guanidine, dodine, dodine-free base, guazatin, guazatin acetate, iminoctadin, iminoctadin triacetate, iminoctadin tris(albesilate), dithianon;

I) Cell Wall Biosynthesis Inhibitors glucan synthesis inhibitors: validamycin, polyoxin B; melanin synthesis inhibitors: pyroquilon, tricyclazole, carpropamid, dicyclomet, fenoxanil;

J) Resistance Inductors acibenzolar-S-methyl, probenazol, isotianil, tiadinil, prohexadione-calcium; phosphonates: fosetyl, fosetyl-aluminum, phosphorous acid and its salts;

K) Unknown Mode of Action bronopol, quinomethionate, cyflufenamid, cymoxanil, dazomet, debacarb, diclomezin, difenzoquat, difenzoquat-methyl sulfate, diphenylamine, fenpyrazamine, flumetover, flusulfamid, flutianil, methasulfocarb, nitrapyrin, nitrothal-isopropyl, oxine-copper, proquinazid, tebufloquin, tecloftalam, triazoxide, 2-butoxy-6-iodo-3-propylchromene-4-one, N-(cyclopropylmethoxyimino-(6-difluoromethoxy-2,3-difluorophenyl)methyl)-2-phenyl-acetamide, N'-(4-(4-chloro-3-trifluoromethylphenoxy)-2,5-dimethylphenyl)-N-ethyl-N-methylformamidine, N'-(4-(4-fluoro-3-trifluoromethylphenoxy)-2,5-dimethylphenyl)-N-ethyl-N-methylformamidine, N'-(2-methyl-5-trifluoromethyl-4-(3-trimethylsilanylpropoxy)phenyl)-N-ethyl-N-methylformamidine, N'-(5-difluoromethyl-2-methyl-4-(3-trimethylsilanylpropoxy)-phenyl)-N-ethyl-N-methylformamidine, N-methyl-(1,2,3,4-tetrahydronaphthalen-1-yl)-2-{1-[2-(5-methyl-3-trifluoromethylpyrazol-1-yl)acetyl]piperidin-4-yl}thiazole-4-carboxamide, N-methyl-(R)-1,2,3,4-tetrahydronaphthalen-1-yl 2-{1-[2-(5-methyl-3-trifluoromethylpyrazol-1-yl)-acetyl]piperidin-4-yl}thiazole-4-carboxamide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, 6-tert.-butyl-8-fluoro-2,3-dimethylquinolin-4-yl methoxyacetate, N-methyl-2-{1-[(5-methyl-3-trifluoromethyl-1H-pyrazol-1-yl)acetyl]piperidin-4-yl}-N-[(1R)-1,2,3,4-tetrahydronaphthalen-1-yl]-4-thiazole-carboxamide, 3-[5-(4-methylphenyl)-2,3-dimethylisoxazolidin-3-yl]-pyridine, 3-[5-(4-chlorophenyl)-2,3-dimethylisoxazolidin-3-yl]-pyridine (pyrisoxazol), N-(6-methoxypyridin-3-yl)cyclopropanecarboxamide, 5-chloro-1-(4,6-dimethoxypyrimidin-2-yl)-2-methyl-1H-benzoimidazole, 2-(4-chlorophenyl)-N-[4-(3,4-di-methoxyphenyl)isoxazol-5-yl]-2-prop-2-ynyloxyacetamide;

M) Growth Regulators abscisic acid, amidochlor, ancymidole, 6-benzylaminopurine, brassinolide, butralin, chlormequat (chlormequat chloride), choline chloride, cyclanilid, daminozide, dikegulac, dimethipin, 2,6-dimethylpuridine, ethephon, flumetralin, flurprimidol, fluthiacet, forchlorfenuron, gibberellic acid, inabenfid, indole-3-acetic acid, maleic hydrazide, mefluidid, mepiquat (mepiquat chloride), metconazole, naphthaleneacetic acid, N-6-benzyladenine, paclobutrazole, prohexadione (prohexadione-calcium), prohydrojasmone, thidiazuron, triapenthenol, tributylphosphorotrithioate, 2,3,5-triiodobenzoic acid, trinexapac-ethyl and uniconazole;

N) Herbicides acetamides: acetochlor, alachlor, butachlor, dimethachlor, dimethenamid, flufenacet, mefenacet, metolachlor, metazachlor, napropamid, naproanilid, pethoxamid, pretilachlor, propachlor, thenylchlor;

amino acid analogs: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

bipyridyls: diquat, paraquat;

carbamates and thiocarbamates: asulam, butylate, carbetamide, desmedipham, dimepiperat, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;
diphenyl ethers: acifluorfen, aclonifen, bifenox, diclofop, ethoxyfen, fomesafen, lactofen, oxyfluorfen;
hydroxybenzonitriles: bromoxynil, dichlobenil, ioxynil;
imidazolinones: imazamethabenz, imazamox, imazapic, imazapyr, imazaquin, imazethapyr;
phenoxyacetic acids: clomeprop, 2,4-dichlorophenoxyacetic acid (2,4-D), 2,4-DB, dichlorprop, MCPA, MCPA-thioethyl, MCPB, mecoprop;
pyrazines: chloridazon, flufenpyr-ethyl, fluthiacet, norflurazon, pyridate;
pyridines: aminopyralid, clopyralid, diflufenican, dithiopyr, fluridone, fluroxypyr, picloram, picolinafen, thiazopyr;
sulfonylureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propylimidazo[1,2-b]pyridazin-3-yl)sulfonyl)-3-(4,6-dimethoxypyrimidin-2-yl)urea;
triazines: ametryne, atrazine, cyanazine, dimethametryne, ethiozine, hexazinone, metamitron, metribuzine, prometryne, simazine, terbuthylazine, terbutryne, triaziflam;
ureas: chlortoluron, daimuron, diuron, fluometuron, isoproturon, linuron, methabenzthiazuron, tebuthiuron;
other acetolactate synthase inhibitors: bispyribac-sodium, cloransulam-methyl, diclosulam, florasulam, flucarbazone, flumetsulam, metosulam, orthosulfamuron, penoxsulam, propoxycarbazone, pyribambenz-propyl, pyribenzoxim, pyriftalide, pyriminobac-methyl, pyrimisulfan, pyrithiobac, pyroxasulfon, pyroxsulam;
others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethyl, chlorthal, cinmethylin, clomazone, cumyluron, cyprosulfamid, dicamba, difenzoquat, diflufenzopyr, Drechslera monoceras, endothal, ethofumesate, etobenzanid, fentrazamide, flumiclorac-pentyl, flumioxazin, flupoxam, fluorochloridon, flurtamon, indanofan, isoxaben, isoxaflutol, lenacil, propanil, propyzamide, quinclorac, quinmerac, mesotrione, methylarsenic acid, naptalam, oxadiargyl, oxadiazone, oxaziclomefon, pentoxazone, pinoxaden, pyraclonil, pyraflufen-ethyl, pyrasulfotol, pyrazoxyfen, pyrazolynate, quinoclamin, saflufenacil, sulcotrione, sulfentrazone, terbacil, tefuryltrione, tembotrione, thiencarbazone, topramezone, 4-hydroxy-3-[2-(2-methoxyethoxy-methyl)-6-trifluoromethylpyridin-3-carbonyl]bicyclo[3.2.1]oct-3-en-2-one, ethyl(3-[2-chloro-4-fluoro-5-(3-methyl-2,6-dioxo-4-trifluoromethyl-3,6-dihydro-2H-pyrimidin-1-yl) phenoxy]pyridin-2-yloxy)acetate, methyl 6-amino-5-chloro-2-cyclopropylpyrimidine-4-carboxylate, 6-chloro-3-(2-cyclopropyl-6-methylphenoxy) pyridazin-4-ol, 4-amino-3-chloro-6-(4-chlorophenyl)-5-fluoropyridin-2-carboxylic acid, methyl 4-amino-3-chloro-6-(4-chloro-2-fluoro-3-methoxyphenyl)pyridin-2-carboxylate and methyl 4-amino-3-chloro-6-(4-chloro-3-dimethylamino-2-fluorophenyl)pyridin-2-carboxylate;

O) Insecticides
organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;
pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;
insect growth inhibitors: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazin; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramate;
nicotine receptor agonists/antagonists: clothianidin, dinotefuran, imidacloprid, thiamethoxam, nitenpyram, acetamiprid, thiacloprid, 1-(2-chlorothiazol-5-ylmethyl)-2-nitrimino-3,5-dimethyl-[1,3,5]triazinane;
GABA antagonists: endosulfan, ethiprole, fipronil, vaniliprole, pyrafluprole, pyriprole, N-5-amino-1-(2,6-dichloro-4-methylphenyl)-4-sulfinamoyl-1H-pyrazole-3-thiocarboxamide;
macrocyclic lactones: abamectin, emamectin, milbemectin, lepimectin, spinosad, spinetoram;
mitochondrial electron transport chain inhibitor (METI) I acaricides: fenazaquin, pyridaben, tebufenpyrad, tolfenpyrad, flufenerim;
METI II and III substances: acequinocyl, fluacyprim, hydramethylnone;
decouplers: chlorfenapyr;
inhibitors of oxidative phosphorylation: cyhexatin, diafenthiuron, fenbutatin oxide, propargite;
insect ecdysis inhibitors: cryomazine;
'mixed function oxidase' inhibitors: piperonyl butoxide;
sodium channel blockers: indoxacarb, metaflumizone;
others: benclothiaz, bifenazate, cartap, flonicamid, pyridalyl, pymetrozin, sulfur, thiocyclam, flubendiamide, chlorantraniliprole, cyazypyr (HGW86); cyenopyrafen, flupyrazofos, cyflumetofen, amidoflumet, imicyafos, bistrifluron and pyrifluquinazone.

The composition according to the invention comprises a water-insoluble pesticide. It may comprise one or more water-insoluble pesticides. The water-insoluble pesticide will in most cases be soluble in water to no more than 10 g/l at 20° C., preferably to no more than 1 g/l and in particular to no more than 0.5 g/l. The skilled worker can simply select pesticides with a suitable solubility from the following pesticide list.

The water-insoluble pesticide usually has a boiling point of above 30° C., preferably above 40° C. and specifically above 45° C.

Preferred water-insoluble pesticides are saflufenacil, dimethenamid-p, pendimethalin, picolinafen, pyraclostrobin, fipronil, metaflumizon, water-insoluble azole fungicides and water-insoluble auxin esters (such as alkyl esters of 2,4-D, for example the 2-ethylhexyl, isobutyl, isooctyl ester of 2,4-D). Water-insoluble azole fungicides can, depending on the desired solubility, be selected among triazoles (such as azaconazole, bitertanol, bromuconazole, cyproconazole, difenoconazole, dini-conazole, diniconazole-M, epoxiconazole, fenbuconazole, fluquinconazole, flusilazol, flutriafol, hexaconazole, imibenconazole, ipconazole, metconazole, myclobutanil, oxpoconazole, paclobutrazol, penconazole, propiconazole, prothioconazole, simeconazole, tebuconazole, tetraconazole, triadimefon, triadimenol, triticonazole, uniconazole); imidazoles (such as cyazofamid, imazalil, imazalil sulfate, pefurazoate, prochloraz, triflumizole); benzimidazoles: benomyl, carbendazim, fuberidazole, thiabendazole; or other azoles (such as ethaboxam, etridiazole, hymexazole, 2-(4-chlorophenyl)-N-[4-(3,4-dimethoxyphenyl)isoxazol-5-yl]-2-prop-2-ynyloxy-acetamid), with the triazoles being preferred.

Preferably, the composition according to the invention comprises a water-soluble agrochemical active substance in addition to the water-insoluble pesticide. It can comprise one or more water-soluble agrochemical active substances. Suitable water-soluble agrochemical active substances are water-soluble pesticides and water-soluble inorganic fertilizers. In most cases, the water-soluble agrochemical active substance is soluble in water to more than 10 g/l at 20° C. Preferably, it is soluble in water to more than 50 g/l, in particular to more than 100 g/l.

The water-soluble pesticide will in most cases be soluble in water to more than 10 g/l at 20° C. Preferably, it is soluble in water to more than 50 g/l, in particular more than 100 g/l. The skilled worker can simply select pesticides with a suitable solubility from the above pesticide list. The water-soluble pesticide is preferably a herbicide and/or a growth regulator, with herbicides being especially preferred. Mixtures of different water-soluble salts of a water-soluble pesticide are likewise possible.

Preferred water-soluble pesticides are glyphosate, glufosinate, 2,4-D, dicamba, paraquat, diquat, chlormequat and mepiquat. Preferred second pesticides are glyphosate (for example as the free acid, the sodium salt, the sesquisodium salt, the potassium salt, the dipotassium salt, the ammonium salt, the diammonium salt, the dimethyl ammonium salt, the trimesium salt or the isopropylamine salt), glufosinate (for example as the ammonium salt), 2,4-D (for example as the ammonium, $C_1$-$C_{12}$-alkylammonium or sodium salt) and dicamba (for example as the diglycolamine, dimethylammonium, diolamine, olamine, potassium, sodium, trolamine salt). The second pesticide especially preferably comprises glyphosate (for example as the potassium salt, ammonium salt, isopropylamine salt).

Examples of inorganic fertilizers are customary fertilizer components, nitrogen sources which may be used being, for example, ammonium sulfate, ammonium nitrate, ammonium chloride, ammonia sulfa-nitrate, urea, cyanamide, dicyandiamide, sodium nitrate, Chile saltpetre or calcium nitrate, and slow-release fertilizers such as oxamide, urea/formaldehyde condensates, urea/acetaldehyde condensates or urea/glyoxal condensates, for example Ureaform, acetylene diurea, isobutylidene diurea or crotonylidene diurea. Compounds which comprise one or more of the plant nutrients phosphorus, potassium, magnesium, calcium or sulfur, and compounds which comprise the trace elements boron, iron, copper, zinc, manganese or molybdenum, may also be present. Examples of such compounds are mono-ammonium phosphate, diammonium phosphate, superphosphate, Thomas meal, triple superphosphate, dicalcium phosphate, potassium phosphate, partially or fully digested crude phosphates, potassium nitrate, potassium chloride, potassium sulfate, dipotassium phosphate, magnesium sulfate, magnesium chloride, kieserite, dolomite, chalk, colemanite, boric acid, borax, iron sulfate, copper sulfate, zinc sulfate, manganese sulfate, ammonium molybdate or similar substances.

The water-soluble inorganic fertilizer is in most cases soluble in water to more 10 g/l at 20° C. Preferably, it is soluble in water to more than 50 g/l, in particular more than 100 g/l. The skilled worker can simply select fertilizers with a suitable solubility from the above fertilizer list. Preferred inorganic fertilizers are sulfates, phosphates or nitrates, in particular ammonium sulfate, ammonium nitrate, and/or ammonium phosphate.

The composition according to the invention usually comprises from 0.5 to 99% by weight, preferably 5 to 85% by weight and in particular 15 to 70% by weight of water-soluble agrochemical active substances such as water-soluble pesticides and/or water-soluble inorganic fertilizers.

The composition according to the invention usually comprises from 0.5 to 70% by weight, preferably 1 to 50% by weight and in particular 1 to 30% by weight water-insoluble pesticide.

The composition according to the invention normally comprises at least 5% by weight, preferably at least 10% by weight, and in particular at least 20% by weight of the water-soluble pesticide or of the water-soluble, inorganic fertilizer. The composition according to the invention normally comprises 1 to 80% by weight, preferably 5 to 65% by weight, and in particular 15 to 45% by weight of the water-soluble pesticide or of the water-soluble, inorganic fertilizer.

The weight ratio of water-insoluble pesticide to alkoxylated polyalkyleneimine can vary within any range, for example in the range of from 1:10 000 to 10 000:1, preferably in the range of from 1:1000 to 1000:1, especially preferably in the range of from 1:100 to 100:1.

The composition according to the invention is preferably present in the form of an agrochemical composition. Usual types of agrochemical compositions are, for example, solutions, emulsions, suspensions, dusts, powders, pastes and granules. Examples of types of compositions here are suspensions (SC, OD, FS), emulsifiable concentrates (EC), emulsions (EW, EO, ES), pastes, pills, wettable powders or dusts (WP, SP, SS, WS, DP, DS) or granules (GR, FG, GG, MG), which can either be soluble or dispersible (wettable) in water, and gels for the treatment of plant propagation materials such as seed (GF). The agrochemical compositions are prepared in the known manner (see for example Mollet, H. and Grubemann, A.: Formulation technology (Wiley VCH Verlag, Weinheim, 2001)).

The agrochemical compositions can furthermore also comprise conventional adjuvants which are conventionally used for plant protection products, the choice of the adjuvants depending on the specific use form or the active substance. Examples of suitable adjuvants are solvents, solid carriers, surface-active substances (such as further solubilizers, protective colloids, wetters and adhesives), organic and inorganic thickeners, bactericides, antifreeze agents, antifoams, optionally colorants and stickers (for example for the treatment of seed).

Suitable solvents are water, organic solvents such as mineral oil fractions of medium to high boiling point such as kerosene, and diesel oil, furthermore coal tar oils and oils of vegetable or animal origin, aliphatic, cyclic and aromatic hydrocarbons, for example paraffins, tetrahydronaphthalene, alkylated naphthalenes and their derivatives, alkylated benzenes and their derivatives, alcohols such as methanol, ethanol, propanol, butanol and cyclohexanol, glycols, ketones such as cyclohexanone, gamma-butyrolactone, dimethyl fatty acid amides, fatty acids and fatty acid esters and strongly polar solvents, for example amines such as N-methyl-pyrrolidone. In principle, it is also possible to use solvent mixtures and mixtures of the abovementioned solvents and water.

Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders or other solid carriers.

Suitable surface-active substances (adjuvants, wetters, adhesives, dispersants or emulsifiers) are the alkali, alkaline-earth, ammonium salts of aromatic sulfonic acids, for example of lignosulfonic acid (Borresperse® types, Borregaard, Norway), phenolsulfonic acid, naphthalenesulfonic acid (Morwet® types, Akzo Nobel, USA) and dibutylnaphthalenesulfonic acid (Nekal® types, BASF, Germany), and of fatty acids, alkyl- and alkylarylsulfonates, alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ethers, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin sulfite waste liquors and proteins, denatured proteins, polysaccharides (for example methylcellulose), hydrophobic-modified starches, polyvinyl alcohol (Mowiol® types, Clariant, Switzerland), polycarboxylates (Sokalan® types, BASF, Germany), polyalkoxylates, polyvinylamine (Lupamin® types, BASF, Germany), polyethyleneimine (Lupasol® types, BASF, Germany), polyvinylpyrrolidone and their copolymers.

Examples of thickeners (i.e. compounds which impart a modified flow behavior to the composition, i.e. high viscosity at rest and low viscosity in the agitated state) are polysaccharides and organic and inorganic layer minerals such as xanthan gum (Kelzan®, CP Kelco, USA), Rhodopol® 23 (Rhodia, France) or Veegum® (R.T. Vanderbilt, USA) or Attaclay® (Engelhard Corp., NJ, USA).

Bactericides may be added to stabilize the composition. Examples of bactericides are those based on dichlorophene and benzyl alcohol hemiformal (Proxel® from ICI or Acticide® RS from Thor Chemie and Kathon® MK from Rohm & Haas) and also isothiazolinone derivatives such as alkylisothiazolinones and benzisothiazolinones (Acticide® MBS from Thor Chemie). Examples of suitable antifreeze agents are ethylene glycol, propylene glycol, urea and glycerol. Examples of antifoams are silicone emulsions (such as, for example, Silikon® SRE, Wacker, Germany, or Rhodorsil®, Rhodia, France), long-chain alcohols, fatty acids, salts of fatty acids, organofluorine compounds and their mixtures. Examples of colorants are pigments, which are sparingly soluble in water, but also dyes, which are soluble in water. Examples of stickers are polyvinylpyrrolidone, polyvinyl acetate, polyvinyl alcohol and cellulose ethers (Tylose®, Shin-Etsu, Japan).

Examples of types of compositions are:
1. Types of compositions for dilution in water
ii) Dispersible concentrates (DC)
   20 parts by weight of the active substances are dissolved in 70 parts by weight of cyclohexanone with addition of 10 parts by weight of a dispersant, for example polyvinylpyrrolidone. Upon dilution in water, a dispersion is obtained. The active substance content is 20% by weight.
iii) Emulsifiable concentrates (EC)
   15 parts by weight of the active substances are dissolved in 75 parts by weight of xylene with addition of calcium dodecylbenzenesulfonate and castor oil ethoxylate (in each case 5 parts by weight). Upon dilution in water, an emulsion is obtained. The composition has an active substance content of 15% by weight.
iv) Emulsions (EW, EO, ES)
   25 parts by weight of the active substances are dissolved in 35 parts by weight of xylene with addition of calcium dodecylbenzenesulfonate and castor oil ethoxylate (in each case 5 parts by weight). Using an emulsifier apparatus (for example Ultra-Turrax), this mixture is placed into 30 parts by weight of water and made into a homogeneous emulsion. Upon dilution in water, an emulsion is obtained. The composition has an active substance content of 25% by weight.
v) Suspensions (SC, OD, FS)
   20 parts by weight of the active substances are comminuted in a stirred ball mill, with addition of 10 parts by weight of dispersants and wetters and 70 parts by weight of water or an organic solvent, to give a fine active substance suspension. Upon dilution in water, a stable suspension of the active substance is obtained. The active substance content in the composition is 20% by weight.
vi) Water-dispersible granules (WG)
   50 parts by weight of the active substances are ground finely, with addition of 50 parts by weight of dispersants and wetters, and prepared as water-dispersible or water-soluble granules by means of technical apparatuses (for example extrusion, spray tower, fluidized bed). Upon dilution in water, a stable dispersion or solution of the active substance results. The compositon has an active susbtance content of 50% by weight.
vii) Water-dispersible powders (WP, SP)
   75 parts by weight of the active substances are ground in a rotor-stator mill with addition of 25 parts by weight of dispersants and wetters and also silica gel. Upon dilution in water, a stable dispersion or solution of the active substance results. The active substance content of the composition is 75% by weight.
viii) Gels (GF)
   In a ball mill, 20 parts by weight of the active substances, 10 parts by weight of dispersant, 1 part by weight of swelling agent and 70 parts by weight of water or of an organic solvent are ground to a fine suspension. Upon dilution with water, a stable suspension with an active substance content of 20% by weight is obtained.

2. Types of compositions for direct application ix) Dusts (DP, DS)

5 parts by weight of the active substances are ground finely and mixed intimately with 95 parts by weight of finely divided kaolin. This gives dust with an active substance content of 5% by weight.

x) Granules (GR, FG, GG, MG)

0.5 part by weight of the active substances are ground finely and combined with 99.5 parts by weight of carriers. Current methods in this context are extrusion, spray drying or the fluidized bed. This gives granules for direct application with an active substance content of 0.5% by weight.

xi) ULV solutions (UL)

10 parts by weight of the active substances are dissolved in 90 parts by weight of an organic solvent, for example xylene. This gives a composition for direct application with an active substance content of 10% by weight.

The composition according to the invention is preferably in the form of an aqueous composition (such as SC), where the water-insoluble pesticide is present in the form of suspended particles. The water content may be at least 10% by weight, preferably at least 30% by weight. The suspended particles may be present in the form of crystalline or amorphous particles which are solid at 20° C. The suspended water-insoluble pesticide usually has a particle size distribution with an $x_{50}$ value of from 0.1 to 10 µm, preferably 0.2 µm to 5 µm and especially preferably 0.5 µm to 2 µm. The particle size distribution can be determined by laser light diffraction of an aqueous suspension comprising the particles. The sample preparation, for example the dilution to the measuring concentration, will, in this measuring method, depend on the fineness and concentration of the active substances in the suspension sample and on the apparatus used (for example Malvern Mastersizer), inter alia. The procedure must be developed for the system in question and is known to a person skilled in the art.

A further subject matter is seed comprising the composition according to the invention. To treat plant propagation materials, in particular seed, it is customary to use water-soluble concentrates (LS), suspensions (FS), dusts (DS), water-dispersible and water-soluble powders (WS, SS), emulsions (ES), emulsifiable concentrates (EC) and gels (GF). These compositions can be applied to the propagation materials, in particular seed, in undiluted or, preferably, diluted form. Here, the composition in question can be diluted 2- to 10-fold so that from 0.01 to 60% by weight, preferably from 0.1 to 40% by weight, of active substance are present in the compositions to be used for seed dressing. The application can be carried out before or during the sowing. The treatment of plant propagation material, in particular treatment of seed, is know to a person skilled in the art and is performed by dusting, coating, pelleting, dipping or immersing the plant propagation material, the treatment preferably being carried out by pelleting, coating and dusting or by the in-furrow treatment, so that for example premature germination of the seed is prevented. It is preferred to use suspensions for the seed treatment. Usually, such compositions comprise from 1 to 800 g/l active substance, from 1 to 200 g/l surfactants, from 0 to 200 g/l antifreeze agents, from 0 to 400 g/l binders, from 0 to 200 g/l colorants and solvents, preferably water.

The active substance concentrations in the ready-to-use preparations can be varied within substantial ranges. In general, they are between 0.0001 and 10%, preferably between 0.01 and 1%. The active substances can also be used successfully in the ultra-low-volume method (ULV), it being possible to apply compositions with more than 95% by weight of active substance, or indeed the active substance without additives. For use in plant protection, the application rates are between 0.001 and 2.0 kg of active substance per ha, preferably between 0.005 and 2 kg per ha, especially preferably between 0.05 and 0.9 kg per ha, in particular between 0.1 and 0.75 kg per ha, depending on the nature of the desired effect. When treating plant propagation materials, for example seed, amounts of active substance of from 0.1 to 1000 g/100 kg of propagation material or seed, preferably from 1 to 1000 g/100 kg, especially preferably from 1 to 100 g/100 kg, in particular from 5 to 100 g/100 kg, will generally be used. When used in the protection of materials or storage materials, the application rate of active substance depends on the nature of the field of application and on the desired effect. Conventional application rates in the protection of materials are, for example, from 0.001 g to 2 kg, preferably from 0.005 to 1 kg, of active substance per cubic meter of treated material.

Substances which may be admixed to the active substances or to the compositions comprising them are various types of oils, or wetters, adjuvants, herbicides, bactericides, other fungicides and/or pesticides, optionally also only just before use (tankmix). These agents can be admixed to the compositions according to the invention in the weight ratio 1:100 to 100:1, preferably 1:10 to 10:1. Adjuvants in this sense which are suitable are, in particular: organically modified polysiloxanes, for example Break Thru S 240®; alcohol alkoxylates, for example Atplus® 245, Atplus® MBA 1303, Plurafac® LF 300 and Lutensol® ON 30; EO-PO block polymers, for example Pluronic® RPE 2035 and Genapol® B; alcohol ethoxylates, for example Lutensol® XP 80; and sodium dioctylsulfosuccinate, for example Leophen® RA.

A further subject is a method of preparing the composition according to the invention by bringing the alkoxylated polyalkyleneimine and the water-insoluble pesticide into contact, for example by mixing. The abovementioned auxiliaries can optionally also be brought into contact with the composition. Further preparation methods for various types of compositions are as described above.

A further object is the use of the alkoxylated polyalkyleneimine for dispersing a water-insoluble pesticide. The polyalkyleneimine is preferably used for suspending. Preferred water-insoluble pesticides are as described above.

The present invention furthermore relates to a method of controlling phytopathogenic fungi and/or undesirable vegetation and/or undesired insect or mite attack and/or for regulating the growth of plants, wherein the composition according to the invention is allowed to act on the respective pests, their environment or the crop plants to be protected from the respective pest, on the soil and/or on undesired plants and/or on the crop plants and/or on their environment. The term crop plants also includes those plants which have been modified by breeding, mutagenesis or recombinant methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such genetic modifications also comprise posttranslational modifications of proteins, oligo- or polypeptides, for example by means of glycosylation or binding of polymers such as, for example, prenylated, acetylated or farnesylated residues or PEG residues.

Advantages of the present invention are, inter alia, that it makes a high storage stability of the formulation possible; that the particle size growth of dispersed agrochemical active substances is slowed down or suppressed; that the agglomeration of dispersed agrochemical particles is slowed down or suppressed; that the settling of dispersed agrochemical active substances is slowed down or suppressed; that the abovementioned advantages are also attained in the presence of high salt concentrations.

The examples which follow illustrate the invention without imposing any limitation.

EXAMPLES

Surfactant A: Anionic surfactant, sodium salt of an alkylnaphthalenesulfonic acid, water-soluble.
Surfactant B: Nonionic surfactant, alkylamine ethoxylate, water-soluble, surface tension (1 g/l water, room temperature) approximately 40 mN/m.

Example 1

Polymer A

An approximately 50% strength aqueous solution of polyethyleneimine (molecular weight 5000 g/mol, GPC; ratio of primary to secondary to tertiary amine was 1:1:0.7 according to $^{13}C$ NMR) was propoxylated (in total 3 mol of propylene oxide per mol of ethyleneimine) and subsequently ethoxylated (27 mol of ethylene oxide per mol of ethyleneimine) as described in example 1 of WO 99/67352. This gave an alkoxylated (3 PO+27 EO) polyethyleneimine (polymer A).

Example 2

Formulation 14 g of pyraclostrobin, 2 g of polymer A from example 1, 2 g of surfactant A, 3.3 g of surfactant B, 13.1 g of glyphosate isopropylammonium salt (60% by weight in water), and 21.6 g of water were weighed into a vessel. 25 ml of glass beads (0.75-1.0 mm) were added, and an aqueous pyraclostrobin suspension was prepared by shaking on a laboratory shaker (4 h, 400 rpm). Thereafter, the glass beads were filtered off.

Example 3

Formulation (Comparative Experiment)

An aqueous suspension of pyraclostrobin was prepared as in example 2, the polymer A of example 1 being replaced by
A) Atlox® 4915, or
B) Copolymer B (acrylic acid/AMPS 70/30).

Atlox® 4913 is a composition comprising 33% by weight of terpolymer (reaction product of methacrylic acid, methyl methacrylate and methoxypolyethylene glycol methacrylate), 33% by weight of propylene glycol, 1% by weight of xylene and 33% by weight of water), HLB value 11-12, commercially available from Uniquema.

The random copolymer B comprises monomers: 70% by weight of acrylic acid and 30% by weight of the sodium salt of acrylamidopropanesulfonic acid (AMPS) incorporated in the polymer.

Example 4

Stability Test of the Suspension

The aqueous suspensions of examples 2, 3A and 3B were stored without agitation for 24 hours at room temperature and thereafter assessed visually with reference to a scale of from 1 (phase separation, no longer dispersible by shaking, clumpy) to 10 (no phase separation, highly viscous, readily dispersible).

TABLE 1

| Formulation of example | Stability assessment |
| --- | --- |
| 2 | 9 |
| 3A[a] | 8 |
| 3B[a] | 2 |

[a]comparative experiment

We claim:
1. An aqueous composition comprising:
a water-insoluble pesticide;
a water soluble agrochemical active substance; and
a nonionic or anionic alkoxylated polyalkyleneimine;
  wherein the water-insoluble pesticide is present in the form of suspended particles and is soluble in water to no more than 1 g/l at 20° C.;
  wherein the water soluble agrochemical active substance comprises from 5% to 85% by weight of the composition, is soluble in water to no more than 10 g/l at 20° C. and is a water-soluble pesticide or a water-soluble inorganic fertilizer,
  wherein the alkoxylated polyalkyleneimine comprises from 0.1% to 25% by weight of the composition, and,
  wherein the water-insoluble pesticide comprises from 1% to 50% by weight of the composition.
2. The composition according to claim 1, wherein the alkoxylated polyalkyleneimine has a molar mass Mw of from 800 to 25 000 g/mol.
3. The composition according to claim 1, wherein the alkoxylated polyalkyleneimine is an ethoxylated and/or propoxylated polyalkyleneimine.
4. The composition according to claim 1, wherein the alkoxylated polyalkyleneimine is an ethoxylated and propoxylated polyalkyleneimine comprising 1 to 50 mol of propylene oxide units and 1 to 50 mol of ethylene oxide units, in each case per mol of NH units.
5. The composition according to claim 1, wherein the alkoxylated polyalkylimine is an ethoxylated and propoxylated polyalkyleneimine comprising 1.5 to 15 mol of propylene oxide units and 10 to 50 mol of ethylene oxide units, in each case per mol of NH units.
6. The composition according to claim 1, wherein the alkoxylated polyalkyleneimine is present in dissolved form.
7. The composition according to claim 1, comprising from 0.5 to 15% by weight of the alkoxylated polyalkyleneimine.
8. Seed treated with the composition according to claim 1.
9. A method of controlling phytopathogenic fungi and/or undesired plant growth and/or undesired insect or mite attack and/or for regulating the growth of plants, wherein the composition according to claim 1 is allowed to act on the respective pests, their environment or the crop plants to be protected from the respective pest, on the soil and/or on undesired plants and/or on the crop plants and/or on their environment.

10. The method of claim 9, wherein the alkoxylated polyalkyleneimine has a molar mass Mw of from 800 to 25 000 g/mol.

11. The method of claim 9, wherein the alkoxylated polyalkyleneimine is an ethoxylated and/or propoxylated polyalkyleneimine.

12. The method of claim 9, wherein the alkoxylated polyalkyleneimine is an ethoxylated and propoxylated polyalkyleneimine comprising 1 to 50 mol of propylene oxide units and 1 to 50 mol of ethylene oxide units, in each case per mol of NH units.

* * * * *